US00PP07904P

United States Patent [19]

van Andel

[11] Patent Number: Plant 7,904

[45] Date of Patent: Jul. 7, 1992

[54] CARNATION NAMES STADIARED

[75] Inventor: Jacob van Andel, Aalsmeer, Netherlands

[73] Assignee: Van Staaveren B.V., Aalsmeer, Netherlands

[21] Appl. No.: 583,791

[22] Filed: Sep. 13, 1990

[51] Int. Cl.[5] ..... A01H 5/00

[52] U.S. Cl. ..... Plt./70.7

[58] Field of Search ..... Plt./70, 73

*Primary Examiner*—Howard J. Locker

*Attorney, Agent, or Firm*—Charles W. Rummler

[57] ABSTRACT

A new and original mini-spray carnation variety particularly distinguished by its small, mainly crimson-colored blossoms, which are borne in a cluster and produced intermittently during its blooming periods. The plant itself is a vigorous-growing bush with a height of about 60 cm.

1 Drawing Sheet

BACKGROUND OF THE NEW PLANT

This new mini-spray carnation cultivar originated as a hybrid seedling developed by me in 1980 at our nursery in Aalsmeer, Holland by crossing two varieties selected from our collection of carnations maintained for breeding purposes at Aalsmeer. This particular seedling was selected for propagation because of its unusual crimson flower coloration and the overall high quality of the plant. Asexual propagation of this selected plant was done by means of cuttings under my direction at Aalsmeer. Propagation of this new plant by cuttings was continued from generation to generation to determine whether the novel characteristics of the selected seedling would be retained from generation to generation and its homogeneity could be assured.

This proved to be successful and this new mini-spray carnation variety is now being propagated at Aalsmeer.

DESCRIPTION OF THE DRAWING

My new mini-spray carnation cultivar is illustrated by the accompanying full-color photographic drawing, which shows blooming portions of spray stems with buds and with flowers, the color rendition being as nearly true to that herein specified as is reasonably possible to obtain by professional photographic procedures.

DESCRIPTION OF THE NEW PLANT

The following is a detailed description of my new mini-spray carnation cultivar variety based upon observation of plants grown in greenhouse as well as outdoors at Aalsmeer and blooming during the current year. The color designations stated herein are according to the R.H.S. COLOUR CHART published by The Royal Horticultural Society of London, England.

THE PLANT

Origin: Seedling.

Parentage:

*Seed parent.*—Plant No. 84583-1 A (unpatented).

*Pollen parent.*—Plant No. 1000-A (unpatented).

Classification:

*Botanic.*—Dianthus hybrid.

*Commercial.*—Mini-spray carnation.

Form: Strong, upright bush with hardly any shoots in the flower stem nodes.

Height: 60 cm, in average.

Main stem:

*Length.*—In average, about 50 cm.

*Growth.*—Vigorous and upright.

*Branching character.*—Hardly any shoots in the flower stem nodes.

Foliage:

*Number of leaves.*—Abundant, depending on season.

*Leaf size.*—About 110 mm long and 10 mm wide at the fifth node.

*Leaf shape.*—Elliptical and curled. Margins: Entire. Texture: Leathery. Color: Both upper and under sides are dark green.

THE BUD

Size: Small.

*Diameter.*—Averaging about 10 mm.

*Length.*—Averaging about 20 mm.

Shape: Cylindrical.

Calyx:

*Shape.*—Oblong.

*Size.*—Averaging about 10 mm in width and 20 mm in length.

*Splitting.*—The calyx does not split.

*Aspect.*—Smooth.

THE FLOWER

Blooming habit: Intermittent, during Spring to Fall blooming seasons.

Size of flower: Small.

*Diameter.—l Averaging about* 40 mm.

*Depth.*—Averaging about 10 mm.

Borne: In a cluster.

Shape:

*When first opening.*—Flat.

*When mature.*—Become somewhat rounded.

Petalage:

*Number of petals.*—Between 15 and 20 in average.

*Texture.*—Soft.

*Color.*—Both outer and inner petals: Body: 52 A. Base: Varies from 52 C to white with occasional streaks of white. Reverse side: 52 D.

Flower stem:

*Length.*—Averaging about 50 cm.

*Color.*—Dark green.

*Character.*—Strong and upright.

Discoloration:

*After full bloom.*—Color becomes somewhat darker.

Persistence: The flowers hang on and dry.

Disease resistance: Resistant to *Fusarium oxysporum.*

Lasting quality: Averaging about 14 days as a cut flower and 21 days on the plant.

REPRODUCTIVE ORGANS

Stamens:

*Number.*—Very few.

*Arrangement.*—Petaloid and rudimental.

*Anthers.*—Size: Small. Color: Beige.

*Filaments.*—Length: About 20 mm. Color: White with pink tops.

*Pollen.*—Color: When present, yellow-brown.

Pistils:

*Number.*—1.

*Styles.*—Length: About 25 mm. Color: White base with pink tips.

Stigma:

*Color.*—Dark pink.

I claim:

1. The new and distinctive mini-spray carnation plant, substantially as herein shown and described, particularly characterized by its crimson-colored flowers, its vigorous and erect growth habit and the intermittent and profuse production of its flowers on strong and upright stems.

* * * * *

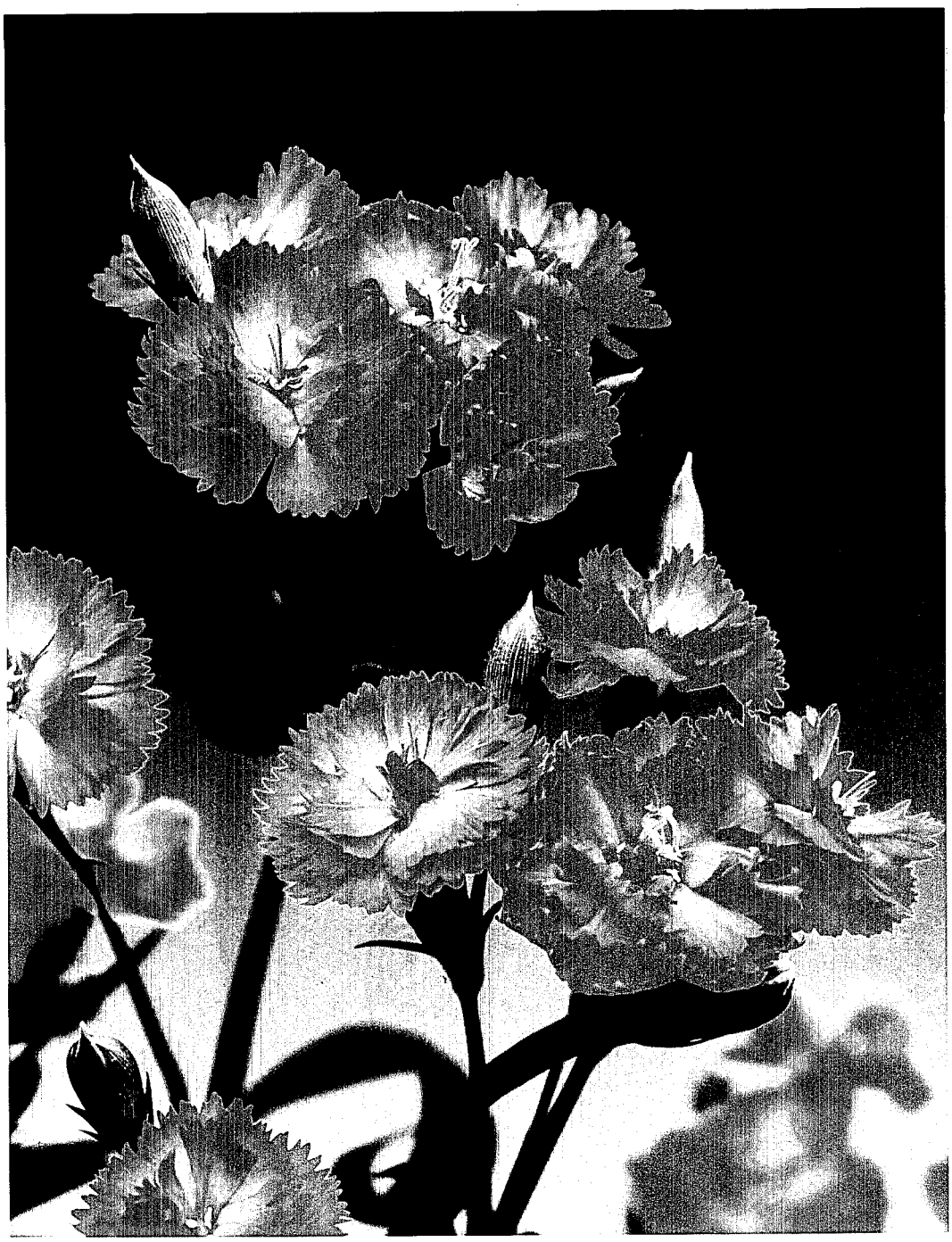

UNITED STATES PATENT AND TRADEMARK OFFICE

CERTIFICATE OF CORRECTION

PATENT NO. : Plant 7,904

DATED : July 7, 1992

INVENTOR(S) : Jacob van Andel

It is certified that error appears in the above-identified patent and that said Letters Patent is hereby corrected as shown below:

On the title page, item [54], please correct the title to read --CARNATION NAMED STADIARED--

Signed and Sealed this

Twenty-first Day of September, 1993

Bruce Lehman

*Attest:*

BRUCE LEHMAN

*Attesting Officer*

*Commissioner of Patents and Trademarks*